United States Patent [19]

Dürr et al.

[11] Patent Number: 4,743,296
[45] Date of Patent: May 10, 1988

[54] HETEROCYCLICALLY FUSED PYRIDINE COMPOUNDS AS HERBICIDES

[75] Inventors: Dieter Dürr, Bottmingen; Hans-Georg Brunner, Lausen; Henry Szczepanski, Wallbach, all of Switzerland

[73] Assignee: Ciba-Geigy Corporation, Ardsley, N.Y.

[21] Appl. No.: 936,214

[22] Filed: Dec. 1, 1986

Related U.S. Application Data

[63] Continuation-in-part of Ser. No. 837,977, Mar. 10, 1986, abandoned.

[30] Foreign Application Priority Data

Mar. 12, 1985 [CH] Switzerland .................. 1111/85
Dec. 20, 1985 [CH] Switzerland .................. 5451/85

[51] Int. Cl.$^4$ .................. A01N 43/40; A01N 43/42; C07D 471/14
[52] U.S. Cl. .................. 71/94; 546/64; 546/82
[58] Field of Search .................. 546/64, 82; 71/94

[56] References Cited

U.S. PATENT DOCUMENTS 4,404,012 9/1983 Orwick et al. .................. 546/82

FOREIGN PATENT DOCUMENTS 0041623 12/1981 European Pat. Off. .............. 546/82
0041624 12/1981 European Pat. Off. .............. 546/82
0133309 2/1985 European Pat. Off. .............. 546/82
0183993 6/1986 European Pat. Off. .............. 546/82

Primary Examiner—Henry R. Jiles
Assistant Examiner—J. Richter
Attorney, Agent, or Firm—Kevin T. Mansfield; Edward McC. Roberts

[57] ABSTRACT

This is a continuation in part application derived from our copending application Ser. No. 837,977 (filing date Mar. 10, 1986). This continuation in part is directed to novel pyridine compounds of formula I below have good selective herbicidal properties pre- and postemergence and also influence or inhibit plant growth. The compounds are of formula I

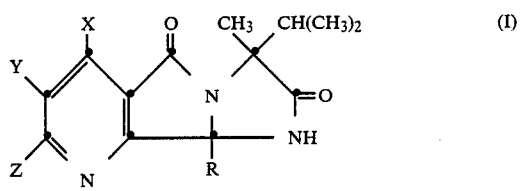

wherein each of X, Y and Z independently of one another is hydrogen or a $C_1$–$C_4$alkyl group, or two adjacent substituents together also form a saturated or unsaturated 3- or 4-membered alkylene chain or alkenyl chain, each of which chains may in turn by substituted by one to four $C_1$–$C_4$alkyl groups, R is a $C_1$–$C_4$nitroalkyl group, a substituted $C_1$–$C_4$alkylthio group or $C_1$–$C_4$alkoxy group, an unsubstituted or substituted $C_3$–$C_4$alkenylthio or $C_3$–$C_4$alkynylthio group, the hydroxyamino group, a $C_1$–$C_4$alkoxyamino, $C_3$–$C_4$alkenyloxyamino or $C_3$–$C_4$alkynyloxyamino group, a —PO($C_1$–$C_4$alkyl)$_2$ or —PO($CH_3$)O$C_1$–$C_4$-alkyl radical or an unsubstituted or substituted hydrazino radical.

12 Claims, No Drawings

HETEROCYCLICALLY FUSED PYRIDINE COMPOUNDS AS HERBICIDES

This is a continuation-in-part of U.S. patent application Ser. No. 837,977 filed Mar. 10, 1986, abandoned.

The present invention relates to novel pyridine compounds with herbicidal and plant growth regulating properties, as well as to the preparation of these novel compounds. The invention also relates to compositions containing the novel imidazolinone compounds, and to methods of using them for selectively controlling weeds or for regulating plant growth.

Specifically, the novel pyridine compounds are derivatives of 3-isopropyl-3-methyl-3H-imidazo[1',2':1,2-]pyrrolo[3,4-b]pyridine-2,5(3H,9bH)-dione, said novel pyridine compounds being of formula I

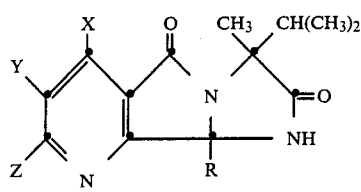

wherein each of X, Y and Z independently of one another is hydrogen or a $C_1$-$C_4$alkyl group, or two adjacent substituents together also form a saturated or unsaturated 3- or 4-membered alkylene chain or alkenylene chain, each of which chains may in turn be substituted by one to four $C_1$-$C_4$alkyl groups; R is a $C_1$-$C_4$alkylthio or $C_1$-$C_4$alkoxy group, each of which groups is substituted in the alkyl moiety by halogen, hydroxy, $C_1$-$C_4$alkoxy, $C_1$-$C_4$alkylthio, $C_1$-$C_4$alkylsulfinyl, $C_1$-$C_4$alkylsulfonyl, cyano, $C_1$-$C_4$alkoxycarbonyl, $C_1$-$C_4$alkylcarbonyl, carboxy, carbamoyl, $C_1$-$C_4$alkylcarbamoyl, di($C_1$-$C_4$alkyl)carbamoyl, carbanilido or phenyl, the phenyl rings being unsubstituted or substituted by halogen, $C_1$-$C_4$alkyl, $C_1$-$C_4$haloalkyl, or $C_1$-$C_4$alkoxy; R is also a $C_3$-$C_4$alkenylthio or $C_3$-$C_4$alkynylthio group, the alkenyl and alkynyl moieties being unsubstituted or substituted in the manner indicated for the above alkyl groups.

In the above definitions, the alkyl, alkenyl and alkynyl groups may be straight chain or branched. Examples of such groups are: methyl, ethyl, ethylene, propyl, propylene, isopropyl, 1- or 2-methylethylene, butyl, butylene, sec-butyl, 1-methylpropylene, isobutyl, 2-methylpropylene, tert-butyl, 2,2-dimethylethylene, 1,2-dimethylethylene, allyl, methallyl, butenyl, propargyl, 2-methylpropynyl and butynyl.

Halogen is fluorine, chlorine, bromine or iodine.

The nomenclature of the imidazo[1',2':1,2]pyrrolo[3,4-b]pyridine system is taken over from Chemical Abstracts; in this text the ring systems are named and numbered as follows:

The basic structure for compounds of formula I is:

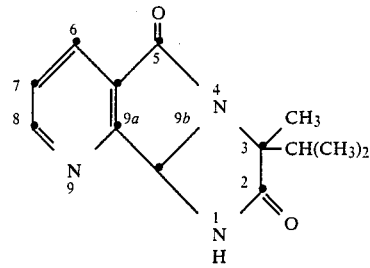

3-Isopropyl-3-methyl-1H-imidazo[1',2':1,2]pyrrolo[3,4-b]pyridine-2,5(3H,9bH)-dione The basic structure for compounds of formula IIa

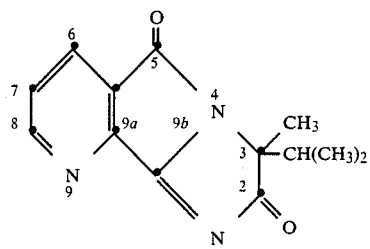

3-Isopropyl-3-methyl-3H-imidazo[1',2':1,2]pyrrolo[3,4-b]pyridine-2,5-dione and for IIb is:

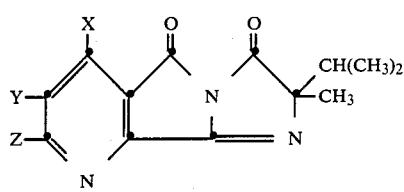

2-Isopropyl-2-methyl-2H-imidazo[1',2':1,2]pyrrolo[3,4-b]pyridine-3,5-dione.

The pyrrolo[3,4-b]pyridine of formula IV and V resp. are named as:

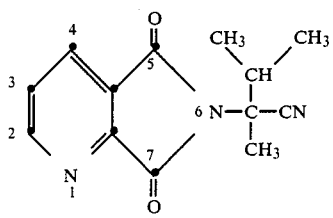

α-[6H-pyrrolo[3,4-b]pyridine-5,7-dione-6-yl]-α-isopropyl-α-methylacetonitrile

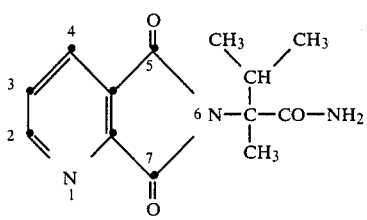

α-[6H-pyrrolo[3,4-b]pyridine-5,7-dione-6-yl]-α-isopropyl-α-methylacetamide.
The preparation of such compounds can be represented by the following scheme:
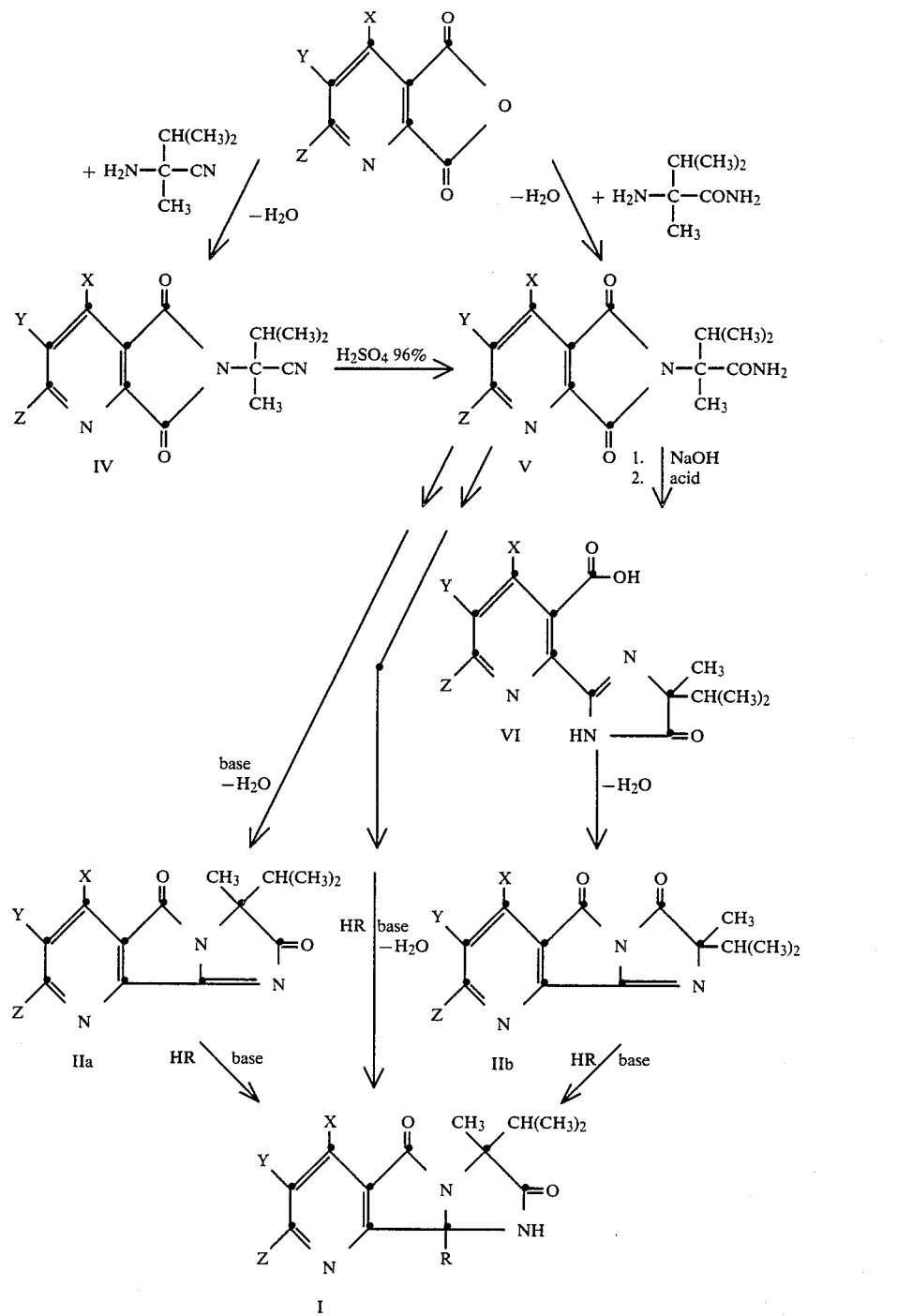
The process of the present invention for the preparation of the imidazolinone compounds of formula I comprises reacting a compound of formula IIa or IIb or of formula V
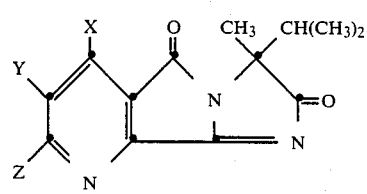
(IIa)

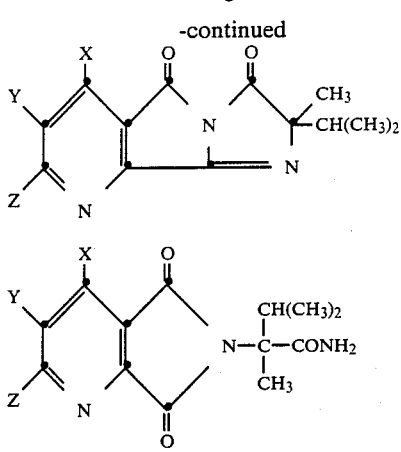

in which formulae X, Y and Z are as defined for formula I, in an inert organic solvent or diluent and in the presence of a base, with a compound of formula III

HR                                 (III)

wherein R is as defined for formula I, and isolating the resultant condensation product from the reaction mixture by acidification with an aqueous acid.

The compounds of formula IIa wherein X, Y and Z are not all hydrogen are novel and constitute an object of this invention.

In said reaction, the compound of formula III is converted in a suitable solvent such as dioxane, tetrahydrofuran or acetonitrile with the starting material of formula IIa or IIb to give the compound of formula I. The reaction is carried out preferably in a basic reaction-medium, it however can also be carried out with an acid catalyst. After dilution with water and acidification with acids, the resultant product is precipitated and isolated by filtration or extracted with a solvent. The compound of formula I can be isolated after the solvent has been evaporated off. The product is obtained in pure form by recrystallization or distillation under a high vacuum.

Certain starting materials of formulae IIa and IIb are known and others may be prepared by known methods.

A pyridine-2,3-dicarboxylic acid α-isopropyl-α-methylacetonitrile of formula V required as starting material can be prepared in simple manner in accordance with the process described in European published application No. 161 221 by condensing an unsaturated hydrazone with a 2-chloro- or 2-bromo-N(α-isopropyl-α-methylacetonitrile)succinimide according to the following scheme

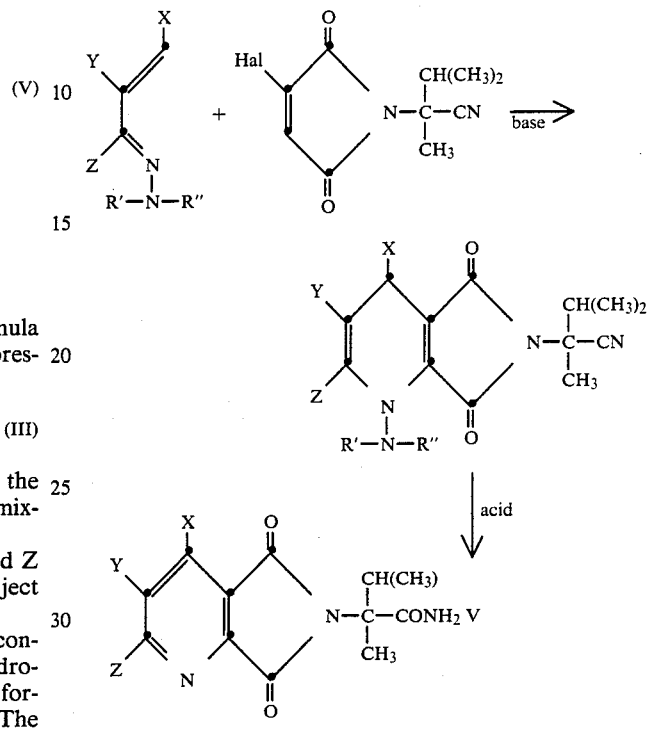

In the above formulae each of R' and R" is hydrogen or $C_1$-$C_4$alkyl, Hal is chlorine or bromine, and X, Y and Z are as defined for formula I.

The starting material of formula V can also be prepared in accordance with the process described in European patent application No. 85 81362.5 by condensing an unsaturated hydrazone with N-(α-isopropyl-α-methylacetonitrile)succinimide. In this reaction, a tetrahydropyridine-2,3-dicarboximide is formed which is converted into the pyridine-2,3-dicarboximide by treatment with silica gel and subsequent oxidation in air according to the following scheme:

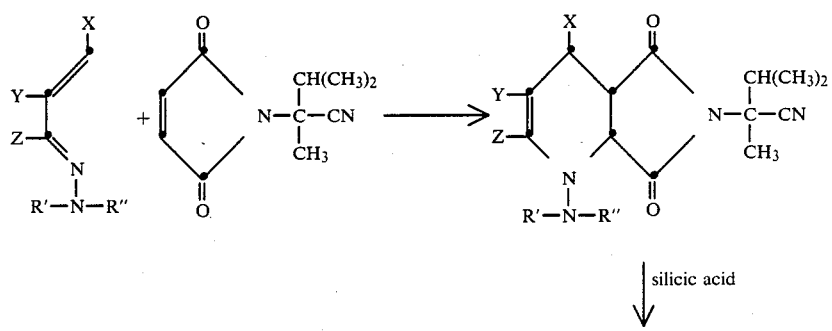

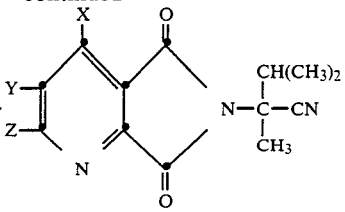 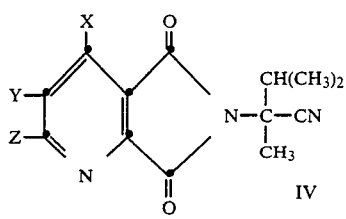

In the above formula each of R' and R" is hydrogen or $C_1$–$C_4$alkyl, and X, Y and Z are as defined for formula I.

If the N-(α-isopropyl-α-methylacetonitrile)-2,3-pyridinedicarboximide of formula IV is first treated with concentrated sulfuric acid, hydrolysis of the nitrile group yields the N-(α-isopropyl-α-methylacetimido)-2,3-pyridinecarboximide of formula V which can be condensed under basic conditions to give the 3-isopropyl-3-methyl-3H-imidazo[1',2':1,2]pyrrolo[3,4-b]pyridine-2,5-dione of formula IIa. The pyridinecarboximide of formula V can also be converted, in the presence of a base such as sodium hydroxide solution, into the 2-(4-isopropyl-4-methyl-5-oxoimidazolidine)nicotinic acid derivative of formula VI which is converted into the starting material of formula IIb (2-isopropyl-2-methyl-3H-imidazo[1',2':1,2]pyrrolo[3,4-b]pyridine-3,5-dione) by treatment with a condensing agent in an organic solvent, with the loss of a water molecule. Nicotinic acids of formula VI and their esters as well as the preparation thereof are described e.g. in European published application No. 41 623.

Examples of suitable condensing agents for this cyclisation are a molar amount of a strong acid, e.g. sulfuric acid, or of anhydride, or a water absorbing reagent such as cyclohexanecarbodiimide, thionyl chloride or phosgene in the presence of a small amount of dimethylformamide. Condensation can also be effected by boiling the reaction mixture in a water separator.

If the reactions can not be carried out at room temperature, then they are carried out in the temperature range from 0° C. to 200° C., i.e. the reaction mixture is heated—if necessary—to its boiling point and cooled—if necessary—with ice/water or ice/brine.

Suitable bases for these condensation or hydrolysis reactions are in particular inorganic bases such as sodium hydroxide, sodium carbonate, calcium hydroxide, calcium carbonate, potassium hydroxide, potassium carbonate, ammonia and tertiary organic bases such as triethylamine.

Suitable solvents are e.g. polar, aprotic solvents which can be used by themselves or in mixtures consisting of at least two solvents. Examples of such solvents are: ethers such as dibutyl ether, tetrahydrofuran, dioxane, methylene glycol, dimethyl ethylene glycol, diethyl diethylene glycol, dimethyl triethylene glycol, halogenated hydrocarbons such as methylene chloride, chloroform, 1-2-dichloroethane, 1,1,1-trichloroethane, 1,1,2,2-tetrachloroethane, carboxylates and lactones such as ethyl acetate, methyl propionate, ethyl benzoate, 2-methoxyethyl acetate, γ-butyrolactone, o-valerolactone and pivalolactone, carboxamides and lactams such as formamide, acetamide, N-methylformamide, N,N-dimethylformamide, N,N-diethylformamide, N,N-dimethylacetamide, N,N-diethylacetamide, γ-butyrolactam, ε-caprolactam, N-methylpyrrolidone, N-acetylpyrrolidone, N-methylcaprolactam, tetramethylurea, hexamethylphosphoric triamide, sulfoxides such as dimethyl sulfoxide, sulfones such as dimethyl sulfone, diethyl sulfone, trimethylene sulfone, tetramethylene sulfone, trimethylamine, N-methylpyrrolidine, N-methylpiperidine, N-methylmorpholine, substituted benzenes such as chlorobenzene, nitrobenzene, nitrobenzene, and nitriles, e.g. acetonitrile.

Preferred compounds of formula I are:
9b-Carboxymethyl-3-isopropyl-3-methyl-1H-imidazo[1',2':1,2]pyrrolo[3,4-b]pyridine-2,5(3H,9bH)-dione,
9b-Allylthio-3-isopropyl-3-methyl-1H-imidazo[1',2':1,2]pyrrolo[3,4-b]pyridine-2,5(3H,9bH)-dione and
9b-Allylthio-7-ethyl-3-isopropyl-3-methyl-1H-imidazo[1',2':1,2]pyrrolo[3,4-b]pyridine-2,5(3H,9bH)-dione.

The invention relates to all diastereomeric and enantiomeric isomers of the compounds of formula I.

The compounds of formula I are usually successfully applied at concentrations of 0.05 to 4 kg/ha, in particular 0.1 to 1 kg/ha.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth regulating, especially growth inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atmoising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oi. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated of unsaturated fatty acids and alkylphenols, said derivatives containing 3 to 10 glycol ether groups and 8 to B 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch" (Handbook of Surfactants), C. Hanser Verlag, Munich & Vienna, 1981.

The compositions usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| compound of formula I: | 1 to 20%, preferably 5 to 10% |
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 90 to 30% |
| surfactant: | 1 to 40%, preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

EXAMPLE 1

Preparation of 3-isopropyl-3-methyl-7-n-propyl-3H-imidazo[1′,2′:1,2-]pyrrolo[3,4-b]pyridine-2,5-dione (starting material)

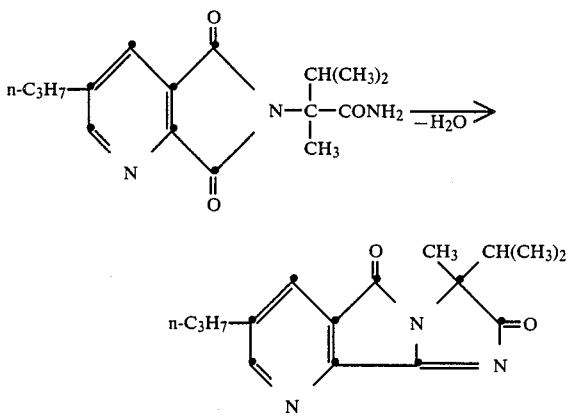

With the simultaneous addition of 0.5 g of powdered sodium hydroxide, a solution of α-[3-n-propyl-6H-pyrrolo[3,4-b]pyridine-5,7-dione-6-yl]-α-isopropyl-α-methyl-acetamide (m.p.: 82° C.) in 100 ml of toluene is heated under reflux for 2 hours in a water separator. After the reaction solution has cooled, it is filtered through silica gel and the filtrate is washed with ethyl acetate and then concentrated by evaporation. The residue is recrystallised from ethyl acetate/petroleum ether, affording 13.1 g of the title compound which melts at 116° C.

The starting materials listed in Table 1 are obtained by following a procedure analogous to that of Example 1.

TABLE 1

IIa (structure with X, Y, Z substituents on pyridine ring fused to pyrrolo-imidazo system with CH3 and CH(CH3)2 groups)

| Comp. | X | Y | Z | phys. data |
|---|---|---|---|---|
| 1.01 | H | nC$_3$H$_7$ | H | m.p. 116° C. |
| 1.02 | H | C$_2$H$_5$ | H | m.p. 119–120° C. |
| 1.03 | H | n-C$_4$H$_9$ | H | m.p. 86–87° C. |
| 1.04 | H | CH(CH$_3$)$_2$ | H | |
| 1.05 | H | CH$_3$ | H | m.p. 102–106° C. |
| 1.06 | C$_2$H$_5$ | CH$_3$ | H | m.p. 128–129° C. |
| 1.07 | ―(CH=CH)$_2$― | — | H | |
| 1.08 | H | ―(CH=CH)$_2$― | — | |
| 1.09 | H | ―(CH$_2$―CH$_2$)$_2$― | — | |
| 1.10 | ―(CH$_2$―CH$_2$)$_2$― | — | H | m.p. 95° C. |
| 1.11 | CH$_3$ | H | CH$_3$ | |
| 1.12 | H | ―(CH$_2$―CH$_2$)$_2$― | — | |
| 1.13 | H | H | CH$_3$ | |
| 1.14 | H | CH$_3$ | CH$_3$ | |
| 1.15 | H | CH(CH$_3$)C$_2$H$_5$ | H | |

EXAMPLE 2

Preparation of 2-isopropyl-2-methyl-7-n-propyl-3H-imidazo[1′,2′:1,2-]pyrrolo[3,4-b]pyridine-3,5-dione (starting material)

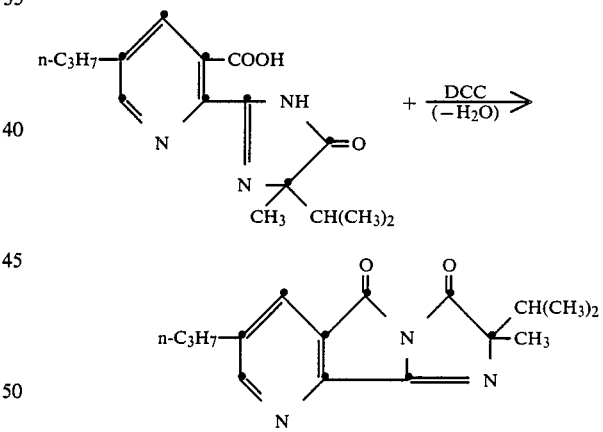

With stirring, 15 g (0.05 mole) of 2-(5-isopropyl-5-methyl-imidazole-3H-4-one-2-yl)-5-n-propylnicotinic acid are added to a solution of 11.1 g of dicyclohexylcarbodiimide in 100 ml of methylene chloride. Stirring is continued for a further 2 hours at room temperature. The resultant dicyclohexylurea is removed by suction filtration and the residue is washed with a small amount of methylene chloride. The filtrate is concentrated by evaporation and the residue is recrystallised from ethyl acetate/hexane, affording the title product in 91% yield (12.1 g) in the form of crystals which melt at 132°–133° C.

The starting materials listed in Table 2 are obtained by following a procedure analogous to that of Example 2.

TABLE 2

IIb

X O O
 \\ ‖ ‖
Y—  — N  CH(CH₃)₂
 /        \\   CH₃
Z        N
 \\     /
  N

| Comp. | X | Y | Z | phys. data |
|---|---|---|---|---|
| 2.01 | H | n-C₃H₇ | H | m.p. 132–133° C. |
| 2.02 | H | CH(CH₃)₂ | H | m.p. 145–146° C. |
| 2.03 | H | C₂H₅ | H | m.p. 136–138° C. |
| 2.04 | H | n-C₄H₉ | H | m.p. 116–119° C. |
| 2.05 | C₂H₅ | CH₃ | H | |
| 2.06 | | —(CH=CH)₂— | H | |
| 2.07 | | —(CH₂—CH₂)₂— | H | |
| 2.08 | H | CH₃ | H | m.p. 129–131° C. |
| 2.09 | H | —(CH=CH₂)— | | |
| 2.10 | H | —(CH₂—CH₂)₂— | | |

EXAMPLE 3

Preparation of
9b-allylthio-3-isopropyl-3-methyl-1H-imidazo[1',2':1,2-]pyrrolo[3,4-b]pyridine-2,5(3H,9bH)-dione

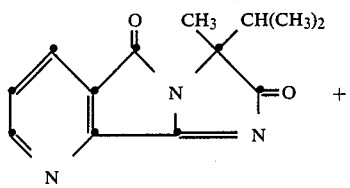

HSCH—CH=CH₂ ⟶

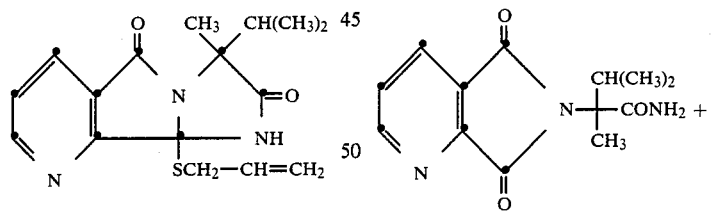

Under a nitrogen atmosphere, 7.8 g of 3-isopropyl-3-methyl-3H-imidazo[1',2':1,2]pyrrolo[3,4-b]pyridine-2,5-dione in 50 ml of tetrahydrofuran are stirred together with 3.5 ml of allylmercaptan and 4.9 ml of triethylamine. The mixture is stirred further for 15 hours at room temperature. In order to work up the reaction mixture, 1.2 ml of formic acid are added and most of the solvent is evaporated off. The residue is chromatographed through a column of silica gel eluted with a 1:1 mixture of ethyl acetate and hexane. The eluant is evaporated off off, leaving a residue which crystallises. Yield: 3.2 g of the title product; m.p.: 126°–138° C.

EXAMPLE 4

Preparation of
9b-allylthio-3-isopropyl-3-methyl-1H-imidazo[1',2':1,2-]pyrrolo[3,4-b]pyridine-2,5(3H,9bH)-dione

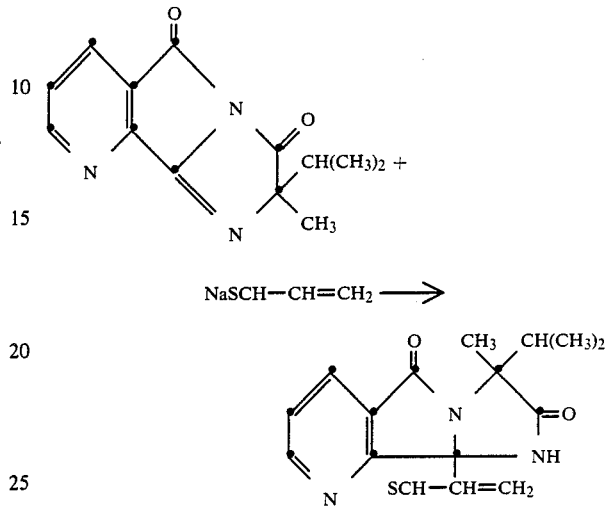

Under a nitrogen atmosphere, 25 ml of allylmercaptan are stirred together with 0.2 g of sodium hydride (80% in white oil). Then 7.3 g of 2-isopropyl-2-methyl-2H-imidazo[1',2':1,2]pyrrolo[3,4-b]pyridine-3,5-dione are stirred in. The reaction mixture is allowed to stand for a relatively long time and is then poured into water. The solution is neutralised with formic acid and then extracted with ethyl acetate. The organic phase is dried and concentrated and the residue is recrystallised from ethylene chloride/hexane. Yield: 4.5 g of the title product; m.p. 126°–128° C.

EXAMPLE 5

Preparation of
9b-allylthio-3-isopropyl-3-methyl-1H-imidazo[1',2':1,2-]pyrrolo[3,4-b]pyridine-2,5(3H,9bH)-dione Under a nitrogen atmosphere, a mixture of 13 g of α-methyl-α-isopropyl-α-[6H-pyrrolo[3,4-b]pyridine-5,7-dion-6-yl]-acetamide in 100 ml of tetrahydrofuran and 4.9 g of sodium allyl thiolate is stirred. After about 15 hours when everything has dissolved, the solution is concentrated by evaporation in vacuo and 2.4 ml of formic acid, 100 ml of ether and 100 ml of water are added to the residue. After stirring for 1 hour, the title product precipitates in crystalline form. The product is isolated by filtration and dried. Yield: 5 g; m.p. 126°-128° C. (decomposition) as in Example 3.

The compounds listed in Table 3 are obtained by following a procedure analogous to those of Example 3 to 5 using corresponding starting materials.

TABLE 3

| Comp. | R⁴ | X | Y | Z | phys. data |
|---|---|---|---|---|---|
| 3.01 | $CH_2-CH=CH_2$ | H | H | H | m.p. 126–128° C. |
| 3.02 | $CH_2-CH=CH_2$ | H | $CH_3$ | H | m.p. 129–131° C. |
| 3.03 | $CH_2-CH=CH_2$ | H | $(n)C_3H_7$ | H | m.p. 135–138° C. |
| 3.04 | $CH_2COOH$ | H | H | H | m.p. 162–165° C. |
| 3.05 | $CH_2-CH_2-COOH$ | H | H | H | m.p. 173–175° C. |
| 3.06 | $CH(COOH)CH_2-COOH$ | H | $CH_3$ | H | m.p. 139–140° C. |
| 3.07 | $CH_2-COOH$ | H | $C_2H_5$ | H | m.p. 170–171° C. |
| 3.08 | $CH_2-COOH$ | H | $C_3H_7$ | H | m.p. 161–162° C. |
| 3.09 | $CH_2-CH_2-COOH$ | H | $C_2H_5$ | H | m.p. 137–138° C. |
| 3.10 | $CH_2-COOH$ | H | $CH_3$ | H | |
| 3.11 | $CH(CH_3)COOH$ | H | $CH_3$ | H | |
| 3.12 | $CH_2-CH_2-COOH$ | H | $CH_3$ | H | |
| 3.13 | $CH(CH_3)-COOH$ | H | $C_2H_5$ | H | |
| 3.14 | $CH_2-COOCH_3$ | H | H | $CH_3$ | |
| 3.15 | $CH_2-COOCH_3$ | H | $CH_3$ | H | |
| 3.16 | $CH_2-COOC_2H_5$ | H | $C_2H_5$ | H | |
| 3.17 | $CH_2-CH_2-COOCH_3$ | H | $CH_3$ | H | |
| 3.18 | $C(CH_3)-COOC_2H_5$ | H | $C_2H_5$ | H | |
| 3.19 | $C(C_2H_5)-COOH$ | H | $CH_3$ | H | |
| 3.20 | $CH_2-CH=CH_2$ | H | $CH_3$ | H | |
| 3.21 | $CH(CH_3)-CH=CH_2$ | H | $CH_3$ | H | |
| 3.22 | $CH_2-C(Cl)=CH_2$ | H | $CH_3$ | H | |
| 3.23 | $CH_2-C(Cl)=CH_2$ | H | $CH_3$ | H | |
| 3.24 | $CH_2-C(CH_3)=CH_2$ | H | $C_2H_5$ | H | |
| 3.25 | $CH_2-C\equiv CH$ | H | $CH_3$ | H | |
| 3.26 | $CH_2-C\equiv CH$ | H | $C_2H_5$ | H | |
| 3.27 | $CH_2-CH=CH-CH_3$ | H | $C_2H_5$ | H | |
| 3.28 | $CH_2-CH=CH_2$ | H | $C_2H_5$ | H | m.p. 138–141° C. |
| 3.29 | $CH_2-COOH$ | H | $-(CH=CH)_2-$ | | m.p. 174–176° C. |
| 3.30 | $CH_2-CH=CH_2$ | H | $-(CH=CH)_2-$ | | |
| 3.31 | $CH_2-C(CH_3)=CH_2$ | H | $-(CH=CH)_2-$ | | |
| 3.32 | $CH_2-CH=CH-CH_3$ | H | $-(CH=CH)_2-$ | | |
| 3.33 | $CH_2-COOC_2H_5$ | H | $-(CH=CH)_2-$ | | |
| 3.34 | $CH_2-CH_2-COOH$ | H | $-(CH=CH)_2-$ | | |
| 3.35 | $CH_2-CH_2-OH$ | H | H | H | |
| 3.36 | $CH_2-CH_2-OH$ | H | $CH_3$ | $CH_3$ | |
| 3.37 | $CH_2-CH_2-OH$ | H | $C_2H_5$ | H | |
| 3.38 | $CH_2-CH_2-OCH_3$ | H | $-(CH=CH)_2-$ | | |
| 3.39 | $CH_2-CO-COOH$ | H | H | $CH_3$ | |
| 3.40 | $CH_2-CH_2-CN$ | H | $CH_3$ | $CH_3$ | |
| 3.41 | $CH_2-CH_2-CN$ | H | $C_2H_5$ | H | |

EXAMPLE 6

Preparation of 9b-carboxylmethoxy-3-isopropyl-3-methyl-1H-imidazo[1',2':1,2]pyrrolo[3,4-b]pyridine-2,5(3H,9bH)-dione

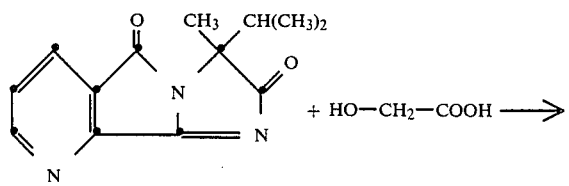

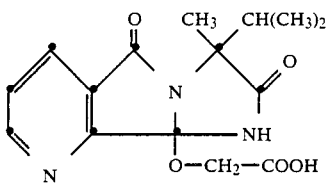

12.2 g of 3-isopropyl-3-methyl-3H-imidazo[1',2':1,2-]pyrrolo[3,4-b]pyridine-2,5-dione and 3.8 g of glycolic acid are heated under reflux for 2 days in 50 ml of tetrahydrofuran. The solvent is subsequently evaporated off and the residue is recrystallised from diethyl ether. Yield: 10.6 g; m.p.: 189°–190° C.

The compounds listed in Table 4 are obtained by following procedure analogous to that of Example 6 using corresponding starting materials.

TABLE 4

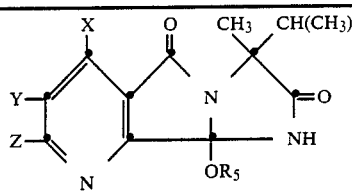

| Comp. | X | Y | Z | R₅ | phys. data |
|---|---|---|---|---|---|
| 4.01 | H | H | H | CH₂—COOCH₃ | |
| 4.02 | H | CH₃ | H | CH₂—COOH | |
| 4.03 | H | C₂H₅ | H | CH₂—COOH | |
| 4.04 | H | CH₃ | H | CH₂—CH₂—COOH | |
| 4.05 | H | C₂H₅ | H | CH₂—CH₂—COOH | |
| 4.06 | H | H | H | CH₂—CH=CH₂ | |
| 4.07 | H | CH₃ | H | CH₂—CH=CH₂ | |
| 4.08 | H | C₂H₅ | H | CH₂—CH=CH₂ | |
| 4.09 | H | —(CH=CH)₂— | | CH₂—COOH | m.p. 229–230° C. |
| 4.10 | H | —(CH=CH)₂— | | C(CH₃)—COOH | |
| 4.11 | H | —(CH=CH)₂— | | CH₂—CH₂—CH₂—COOCH₃ | |
| 4.12 | H | CH₃ | H | CH₂—CH₂—Cl | |
| 4.13 | H | C₂H₅ | H | CH₂—CH₂—CN | |
| 4.14 | H | H | CH₃ | CH₂—CH₂—N(CH₃)₂ | |
| 4.15 | H | CH₃ | H | CH₂—CH₂—SCH₃ | |
| 4.16 | H | C₂H₅ | H | CH₂—CO—CH₃ | |
| 4.17 | H | CH₃ | H | CH₂—CO—N(CH₃)₂ | |
| 4.18 | H | C₂H₅ | H | CH₂—CH₂—OC₂H₅ | |
| 4.19 | H | CH₃ | H | CH₂—CH₂—OCH₃ | |
| 4.20 | H | C₂H₅ | H | CH₂—CH₂—CH₂—OH | |
| 4.21 | H | CH₃ | H | CH₂—CH₂—O—CO—CH₃ | |
| 4.22 | H | C₂H₅ | H | CH₂—CH₂—Cl | |

Formulation Examples

EXAMPLE 7

Formulation Examples for compounds of formula I
(percentages are by weight)

| (a) Wettable powders | (a) | (b) | (c) |
|---|---|---|---|
| compound of Tables 3 to 4 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of Tables 3 to 4 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Tables 3 to 4 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulate | (a) | (b) |
|---|---|---|
| compound of Tables 3 to 4 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a steam of air.

| (e) Coated granulate | |
|---|---|
| compound of Tables 3 to 4 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of Tables 3 to 4 | 40% | 5% |
| ethylene glycol | 10% | 10% |
| nonylphenol polyethylene glycol ether (15 moles of ethylene oxide) | 6% | 1% |

-continued

| (f) Suspension concentrate | (a) | (b) |
|---|---|---|
| sodium lignosulfonate | 10% | 5% |
| Zcarboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Tables 3 to 4 | 5% |
| isopropylamine | 1% |
| octylphenol polyethylene glycol ether (78 moles of ethylene oxide) | 3% |
| water | 91% |

Biological Examples

EXAMPLE 8

Preemergence herbicidal action

In a greenhouse, immediately after sowing the test plants in seed dishes, the surface of the soil is treated with an aqueous dispersion of the test compounds, obtained from a 25% emulsifiable concentrate. Concentrations of 4 kg of test compound per hectare are applied. The seed dishes are kept in the greenhouse at 22°–25° C. and 50% relative humidity. The test is evaluated 3 weeks later in accordance with the following rating:
1: plant has not germinated or it has died
2–3: very severe damage
4: severe damage
5: moderate damage, stunted growth
6: damage, the plant can regenerate
7–8: slight damage
9: normal growth, as untreated plants In this test, the compounds of Tables 3 to 4 exhibit strong herbicidal activity. A number of results are given in Table 6.

TABLE 6

| Compound | Avena | Setaria | Sinapsis | Stellaria |
|---|---|---|---|---|
| 3.01 | 2 | 2 | 2 | 2 |

EXAMPLE 9

Postemergence herbicidal action (contact herbicide)

A number of weeds, both mono- and dicotyledonous, are sprayed postemergence in the 4- to 6-leaf stage with an aqueous active ingredient dispersion at a rate of 4 kg of test compound per hectare and kept at 24°–26° C. and 45–60% relative humidity. The test is evaluated 15 days later in accordance with the same rating as employed above. In this test, the compounds of Tables 3 to 4 also exhibit strong to very strong herbicidal activity. A number of results are given in Table 7.

TABLE 7

| Compound | Avena | Setaria | Lolium | Solanum | Sinapsis | Stellaria |
|---|---|---|---|---|---|---|
| 3.01 | 1 | 2 | 2 | 1 | 2 | 2 |

EXAMPLE 10

Preemergence herbicidal action

Plastic pots are filled with expanded vermiculite (density: 0.135 g/cm$^3$; water-absorbing capacity: 0.565 1/1). After the non-adsorptive vermiculite has been saturated with an aqeuous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis.* The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0,5% of a commercial liquid fertiliser (Greenzit ®) is added to the water. The test is evaluated 12 days after sowing and the action on the plants is assessed in accordance with the rating indicated in Example 8.

The results are given in Table 8:

TABLE 8

| Comp. | Rate of application ppm | Nasturtium officinalis | Agrostis tenuis | Stellaria media | Digitaria sang. |
|---|---|---|---|---|---|
| 3.01 | 100 | 2 | 2 | 2 | 2 |
| | 10 | 2 | 2 | 2 | 2 |
| | 1 | 2 | 2 | 2 | 3 |
| | 0.1 | 3 | 3 | 3 | 3 |
| | 0.01 | 4 | 4 | 4 | 4 |

EXAMPLE 11

Herbicidal action in wild rice (paddy)

The weeds *Echinocloa crus galli* and *Monocharia vag.*, which occur in water, are sown in plastic beakers (surface: 60 cm$^2$; volume: 500 ml). After sowing, the beakers are filled with water up to the surface of the soil. 3 days after sowing, the water level is increased to slightly above the soil surface (3–5 mm). Application is effected 3 days after sowing by spraying the beakers with an aqueous emulsion of the test compounds. The rate of application corresponds to a concentration of 4 kg of active ingredient per hectare (concentration of the spray mixture = 550 1/ha). The beakers are then kept in the greenhouse under optimum growth conditions for rice weeds, i.e. at 25°–30° C. and at high humidity. The evaluation of the tests takes place 3 weeks after application.

Evaluation is made in accordance with the linear rating indicated in Example 8.

The results are given in Table 9:

TABLE 9

| Compound | *Echinochloa crus* galli | *Monocharia vag.* |
|---|---|---|
| 3.01 | 3 | 1 |

EXAMPLE 12

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test, a marked reduction in new growth of the plants treated with compounds of Tables 3 to 4 at concentrations of 50 to 3000 g/ha is observed (less than 20% of the new growth of untreated control plants), without damage being caused to the test plants.

EXAMPLE 13

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after abut 5 weeks by optimum control of temperature, light, fertiliser addition, and watering. The plants are then sprayed with an aqueous mixture of a compound of Tables 3 to 9 until thoroughly wetted. The concentration corresponds to up to 100 g a.i. per hectare. Evaluation is made about 5 weeks after application.

Compared with untreated controls, the compounds of Tables 3 to 4 of the invention markedly increase the number and weight of the harvested siliquae on the leading shoot.

EXAMPLE 14

Growth inhibition of cereals

Summer barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of Tables 3 to 4. The concentration corresponds to up to 100 g of active ingredient per hectare. Evaluation of the growth of the cereals is made 21 days after application. A comparison with untreated controls show that the growth of treated cereal plants is reduced (60-90% of the controls) and that the diameter of the stalks has in some cases increased.

EXAMPLE 15

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Tables 3 to 4. The concentration of test compound corresponds to a rate of application of up to 500 g a.i. per hectare. The growth of the grasses is evaluated 21 days after application. The test compounds of Tables 3 to 5 effect a reduction in new growth in the range of 10-30% in comparison with untreated controls.

EXAMPLE 16

Desiccation and defoliation action

Cotton plants of the Delapine variety are reared in earthen-ware pots in a greenhouse. After the capsules have formed, the plants are sprayed with an aqueous formulation of a compound of Tables 3 to 5 at rates of application corresponding to 1.2, 0.6 and 0.3 kg/ha in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant).

In this test, plants treated with test compounds of Tables 3 to 4 at rates of application of 0.6 and 1.2 kg/ha are left after 7 days with only a few dried out leaves (<80% defoliation and dessication).

What is claimed is:

1. A pyridine compound of formula I

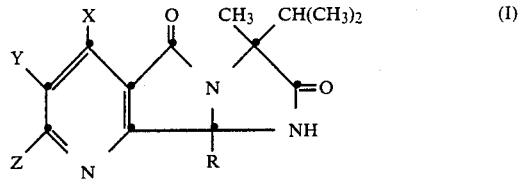

wherein each of X, Y and Z independently of one another is hydrogen or a $C_1$-$C_4$alkyl group, or two adjacent substituents together also form a saturated or unsaturated 3- or 4-membered alkylene chain or alkenylene chain, each of which chains may in turn be substituted by one to four $C_1$-$C_4$alkyl groups; R is a $C_1$-$C_4$alkylthio or $C_1$-$C_4$alkoxy group, each of which groups is substituted in the alkyl moiety by halogen, hydroxy, $C_1$-$C_4$alkoxy, $C_1$-$C_4$alkylthio, $C_1$-$C_4$alkylsulfinyl, $C_1$-$C_4$alkylsulfonyl, cyano, $C_1$-$C_4$alkoxycarbonyl, $C_1$-$C_4$alkylcarbonyl, carboxy, carbamoyl, $C_1$-$C_4$alkylcarbamoyl, di($C_1$-$C_4$alkyl)carbamoyl or carbanilido; R is also a $C_3$-$C_4$alkenylthio or $C_3$-$C_4$alkynylthio group, the alkenyl and alkynyl moieties being unsubstituted or substituted in the manner indicated for the above alkyl groups.

2. A compound according to claim 1, wherein R is a substituted $C_1$-$C_4$alkoxy radical, and X, Y and Z are as defined in claim 1.

3. 9b-Carboxymethoxy-3-isopropyl-3-methyl-1H-imidazo[1',2':1,2]pyrrolo[3,4-b]pyridine-2,5(3H,9bH)-dione according to claim 1.

4. A compound according to claim 1, wherein R is a $C_3$-$C_4$alkenylthio radical and X, Y and Z are as defined in claim 1.

5. 9b-Allylthio-3-isopropyl-3-methyl-1H-imidazo[1'2':1,2]pyrrolo[3,4-b]pyridine-2,5(3H,9bH)-dione according to claim 1.

6. 9b-Allylthio-7-ethyl-3-isopropyl-3-methyl-1H-imidazo[1',2':1,2]pyrrolo[3,4-b]pyridine-2,5(3H,9bH)-dione according to claim 1.

7. A herbicidal and plant growth regulating composition which contains, as active ingredient a herbicidally or plant growth regulatingly effective amount of a compound according to claim 1, together with a carrier or other adjuvant.

8. A method of controlling undesired plant growth, which method comprises the application of a herbicidally effective amount of a compound according to claim 1, or of a composition containing such a compound to said plants or their locus.

9. A method of inhibiting plant growth, which method comprises the application of a growth-inhibitingly effective amount of a compound according to claim 1, or of a composition containing such a compound to said plants postemergence.

10. A method of influencing plant growth for increasing the yield, which method comprises the application of a yield-increasingly effective amount of a compound according to claim 1, or of a composition containing such a compound to said plants postemergence.

11. A method of selectively controlling weeds pre- or postemergence in crops of useful plants, which method comprises treating said useful plants or the crop areas thereof with a herbicidally effective amount of an imidazolinone compound of formula I according to claim 1, or of a composition containing such a compound.

12. A method of suppressing plant growth beyond the 2-leaf stage, which method comprises treating the plants during their growth with a growth-suppressingly effective amount of an imidazolinone compound of formula I according to claim 1, or of a composition containing such a compound.

* * * * *